US00PP18043P2

(12) United States Plant Patent
Hanes

(10) Patent No.: US PP18,043 P2
(45) Date of Patent: Sep. 18, 2007

(54) ***PELARGONIUM* PLANT NAMED 'FREE DEROSE'**

(50) Latin Name: *Pelargonium peltatum*
Varietal Denomination: Free Derose

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/369,657

(22) Filed: Mar. 7, 2006

(51) Int. Cl.
*A01H 5/00* (2006.01)

(52) U.S. Cl. ..... Plt./332
(58) Field of Classification Search ..... Plt./332
See application file for complete search history.

*Primary Examiner*—Anne Marie Grunberg
*Assistant Examiner*—Georgia Helmer
(74) *Attorney, Agent, or Firm*—Jondle & Associates, P.C.

(57) ABSTRACT

A new *pelargonium* plant particularly distinguished by cherry-red, double flowers, floriferous with medium-sized inflorescence, grass-green foliage with weak to medium zonation, a medium to tall, round and well-branched plant habit with a mid-season flowering response, is disclosed.

1 Drawing Sheet

Genus and species: *Pelargonium peltatum* L'Héritier.
Variety denomination: 'Free Derose'.

BACKGROUND OF THE NEW PLANT

The present invention comprises a new and distinct cultivar of *pelargonium,* botanically known as a *Pelargonium peltatum* L'Héritier, and hereinafter referred to by the cultivar name 'Free Derose'. The new cultivar was propagated from a seedling resulting from the cross of the female parent '9120-3', a magenta-flowered proprietary *pelargonium* plant (unpatented) and the male parent 'Free Cherry Rose' (U.S. Plant Pat. No. 12,448) a commercial *pelargonium* plant having cherry-rose flowers.

The new cultivar was created in 2001 in Gilroy, Calif. and has been asexually reproduced repeatedly by vegetative cuttings and tissue culture in Gilroy, Calif. and Hillscheid, Germany over a three-to four-year period. The present invention has been found to retain its distinctive characteristics through successive asexual propagations.

Plant Breeder's Rights for this cultivar were applied for in Canada on Mar. 29, 2005 and with the European Union on Sep. 20, 2005.

SUMMARY OF THE INVENTION

The following are the most outstanding and distinguishing characteristics of this new cultivar when grown under normal horticultural practices in Gilroy, Calif. and Hillscheid, Germany.

1. Cherry-red, double flowers;
2. Floriferous with medium-sized inflorescences;
3. Grass-green foliage with weak to medium zonation;
4. Medium to tall-sized plant habit;
5. A rounded and well-branched plant habit; and
6. About a mid-season flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph is of an above view of three 22-week-old plants grown in a greenhouse in mid-Summer in Hillscheid, Germany.

DESCRIPTION OF THE NEW CULTIVAR

The following detailed description sets forth the distinctive characteristics of 'Free Derose'. The data which define these characteristics were collected from asexual reproductions carried out in Hillscheid, Germany. The plant history was taken on 13-week old plants which were planted as rooted cuttings in 12-cm pots in late May 2005 and grown in a greenhouse. The plants were pinched once. Color readings were taken under natural light in mid-May from flowers grown in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Geraniaceae.
- *Botanical.*—*Pelargonium peltatum* L'Héritier.
- *Common name.*—Ivy geranium.

Parentage:
- *Female parent.*—'9120-3' a proprietary magenta-flowered *pelargonium* plant (unpatented).
- *Male parent.*—'Free Cherry Rose', a commercial *pelargonium* plant having cherry-rose flowers (U.S. Plant Pat. No. 12,448).

Growth:
- *Form.*—Shrub, self-branching, rounded shape.
- *Branching habit.*—9 to 11 branches per plant.
- *Height* (*measured from the top of the soil, excluding the inflorescence*).—15.0 cm.
- *Width* (*horizontal plant spread*).—34.0 cm.
- *Plant size in late summer* (*plant radius, measured from the plant base to the tips*).—30 week-old plant developed branches of 55 cm in length.

*Time to produce a finished flowering plant.*—About 11 to 12 weeks for a 12-cm to 14-cm pot in the Spring.

*Outdoor plant performance.*—Plants continuously flower; a count in early September of 30-week old plants in Hillscheid, Germany produced about 20 to 25 inflorescences per plant.

*Time to initiate and develop roots.*—About 24 days at 20° C.

*Root description.*—Fibrous.

Leaves:

*Arrangement.*—Usually opposite at flowering branches.

*Immature leaf color.*—Upper surface: RHS 143A (grass-green). Lower surface: RHS 143B.

*Mature leaf color.*—Upper surface: From RHS 137D to RHS 143A (medium-green). Lower surface: RHS 143B.

*Size.*—Length: 5.3 cm. Width: 9.4 cm.

*Apex.*—Rounded.

*Base.*—Cordate.

*Shape.*—Ivy-shaped, with distinct lobes and with the gap between the lowest lobes mostly closed.

*Margin.*—Partly crenate.

*Texture.*—Leathery. Upper surface: Smooth, glossy and glabrous. Lower surface: Protruding veins in palmate arrangement.

*Zonation color.*—RHS 166A (brown), weak to medium distinctness.

*Zonation diameter.*—About 3 cm, a relatively narrow ring or belt.

*Venation type.*—Palmate.

*Venation color.*—RHS 145A.

*Petioles.*—Color: RHS 143C (light-green). Length: 3 cm to 5 cm. Diameter: 0.2 cm. Texture: Glabrous.

Stems:

*Number of branches per plant.*—9 to 11.

*Stem color.*—RHS 143C (light-green).

*Length.*—20.3 cm.

*Diameter (at the midpoint).*—0.4 cm.

*Internode length.*—2.0 cm to 4.5 cm.

*Texture.*—Smooth, glabrous.

Inflorescence bud:

*Shape.*—Elliptical.

*Size.*—Length: 1.5 cm. Width: 1.0 cm.

*Color of sepals (just before petals unfold).*—RHS 143A.

*Color of petals (just before petals unfold).*—RHS 58B to RHS 58C.

Inflorescence:

*Blooming habit.*—Continuous from Spring to Fall.

*Inflorescence type.*—An umbel composed of 10 to 15 flowers.

*Umbel.*—Shape: Semi-spherical or nearly semi-spherical. Diameter: 8.7 cm. Height (depth): 5.5 cm.

*Lastingness of umbel on the plant.*—About 16 to 18 days.

*Flowering response.*—Average of 1 open inflorescence 13 weeks after planting rooted cuttings.

*Lastingness of individual flowers on plant.*—6 to 7 days at 18° C.

*Fragrance.*—None.

*Peduncle.*—Color: RHS 143B (light-green). Length: 12.6 cm. Diameter: 0.3 cm. Texture: Glabrous.

*Pedicel.*—Color: Upper surface: RHS 178A (brown). Lower surface: RHS 143A (green). Length: 2.8 cm. Diameter: 0.1 cm. Texture: Weak, short pubescence.

Corolla:

*Shape of corolla.*—Oval outline with both the upper petals somewhat longer than the lower petals.

*Form.*—Double.

*Diameter.*—5.3 cm.

*Number of petals.*—12 to 18.

*Petaloids.*—Shape: Threadlike or like small petals. Number: 1 to 5. Color: Upper surface: RHS N57B to RHS N57C, the petal color or a little lighter. Lower surface: RHS 155A (whitish).

Petals:

*Shape.*—Obovate or spatulate.

*Apex.*—Rounded.

*Base.*—Attenuate or acute.

*Margin.*—Entire.

*Texture.*—Smooth, slightly glossy.

*Upper petals.*—Length: 2.8 cm to 3.0 cm. Width: 2.1 cm to 2.6 cm. Color: Upper surface: Near RHS N57A or slightly more reddish. Lower surface: About RHS 61D or lighter. Markings: Dark-red veins and a small dot, all RHS 53A.

*Lower petals.*—Length: 2.6 cm. Width: 1.9 cm to 2.0 cm. Color: Upper surface: RHS N57B. Lower surface: Near RHS 61D. Markings: Absent.

Sepals:

*Number.*—5.

*Color.*—RHS 143C for both surfaces, the largest sepal has some anthocyanin, RHS 179A (brown) on the upper surface and RHS 179B for the lower surface.

*Length.*—1.3 cm.

*Width.*—Largest upper sepal: 0.5 cm. Other sepals: 0.3 cm.

*Shape.*—Ensiform or ligulate.

*Apex.*—Acute.

*Base.*—Fused.

*Margin.*—Entire.

*Texture.*—Sparse, long, thin hairs.

Reproductive organs:

*Androecium.*—Number of anthers: 3 to 5. Filament color: RHS 155A (whitish). Filament length: 1.0 cm. Filament diameter: 0.1 cm. Pollen color: RHS 26A (orange). Pollen amount: Moderate.

*Gynoecium.*—Pistil: Number: 1. Length: 0.9 cm. Diameter (at the midpoint): 0.1 cm. Stigma color: RHS 58D (pink). Stigma shape: 5 to 6-lobed, lobes at right angles to the style. Style color: RHS 155A (whitish). Style length: 0.3 cm to 0.4 cm. Style shape: Filiform (filament-like) with the lobes of the stigma at right angles.

Fruit and seed set: No seed set observed.

Disease and insect resistance: No particular resistance or susceptibility has been observed.

COMPARISON WITH PARENTAL AND COMMERCIAL CULTIVARS

'Free Derose' differs from the female parent '9120-3' (unpatented) by having cherry-red flowers, while '9120-3' has magenta flowers. In addition, 'Free Derose' has no seed set and has a finer plant structure than '9120-3'.

'Free Derose' differs from the male parent 'Free Cherry Rose' (U.S. Plant Pat. No. 12,448) by having deeper cherry-red flowers than 'Free Cherry Rose'. In addition, 'Free Derose' has a stronger leaf zonation and a taller plant habit than 'Free Cherry Rose'.

'Free Derose' differs from the commercial variety 'Fislamda' (U.S. Plant Pat. No. 12,225) by having less bluish flowers than 'Fislamda'. In addition, 'Free Derose' has smaller inflorescences, shorter peduncles and a shorter plant habit than 'Fislamda'.

I claim:

1. A new and distinct cultivar of *pelargonium* plant as shown and described herein.

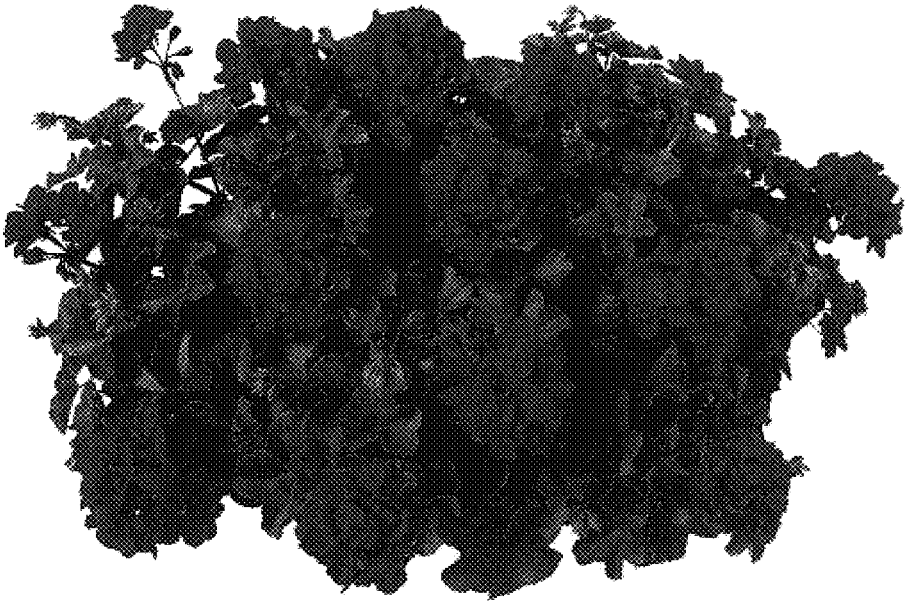

* * * * *